United States Patent [19]

Clark, Jr. et al.

[11] Patent Number: 4,725,883
[45] Date of Patent: Feb. 16, 1988

[54] OPTICAL PROFILOMETRY SYSTEM FOR TUBULAR PRODUCTS

[75] Inventors: William G. Clark, Jr., Murrysville; Lee W. Burtner; Francis X. Gradich, both of Elizabeth, all of Pa.

[73] Assignee: Westinghouse Electric Corp., Pittsburgh, Pa.

[21] Appl. No.: 886,844

[22] Filed: Jul. 18, 1986

[51] Int. Cl.⁴ .............................................. H04N 7/18
[52] U.S. Cl. .................................... 358/100; 358/98; 358/106; 356/241
[58] Field of Search .................. 358/100, 106, 98, 93; 356/241, 237

[56] References Cited

U.S. PATENT DOCUMENTS

| | | | |
|---|---|---|---|
| 2,712,697 | 7/1955 | Lebourg . | |
| 3,739,089 | 6/1973 | Latall | 358/100 |
| 3,761,186 | 9/1973 | Wason | 356/241 |
| 4,072,427 | 2/1978 | Alsberg | 358/106 |
| 4,275,414 | 6/1981 | Norris | 356/241 |
| 4,317,632 | 3/1982 | Orphan et al. | 356/241 |
| 4,403,860 | 9/1983 | Pryor | 356/375 |
| 4,440,496 | 4/1984 | Milana | 356/241 |
| 4,460,920 | 7/1984 | Weber | 358/100 |

FOREIGN PATENT DOCUMENTS

| | | | |
|---|---|---|---|
| 50255 | 4/1977 | Japan | 356/241 |
| 569400 | 5/1945 | United Kingdom . | |
| 123330 | 11/1958 | U.S.S.R. | 356/241 |

OTHER PUBLICATIONS

Optical Technique for Internal Diametrical Measurement of Steam Generator Tubes, Epri Final Report, Nov. 1979, Prepared by Sigma Research, Inc., pp. 1 to 29.
Western Electric Technical Digest, No. 19, Jul. 1970, Method of Checking Wall Imperfections, by A. Heinz, pp. 31-32.
Sigma Optical Profilometer-When Tube Distortion Can Shut Down Operation, Sigma Research, Inc., 1983.

Primary Examiner—Tommy P. Chin

[57] ABSTRACT

An optical inspection system for tubular products utilizes a feeler for engaging the internal surface of the tube to be inspected and a miniature charge coupled device video camera for viewing the interface between the feeler and the tube. An image processing computer responsive to the output of the video camera produces information for rapidly assessing damage or distortion of the tube. The camera is pulled or pushed through the tube while continuously monitoring the optical contrast between the feeler and the tube wall. The camera image of the tube ID is fed to the image processing computer to determine and record changes in ID contour is a function of the axial position of the camera and feeler. These data in turn can be used in tubing life prediction considerations. The data may be analyzed manually if desired.

18 Claims, 12 Drawing Figures

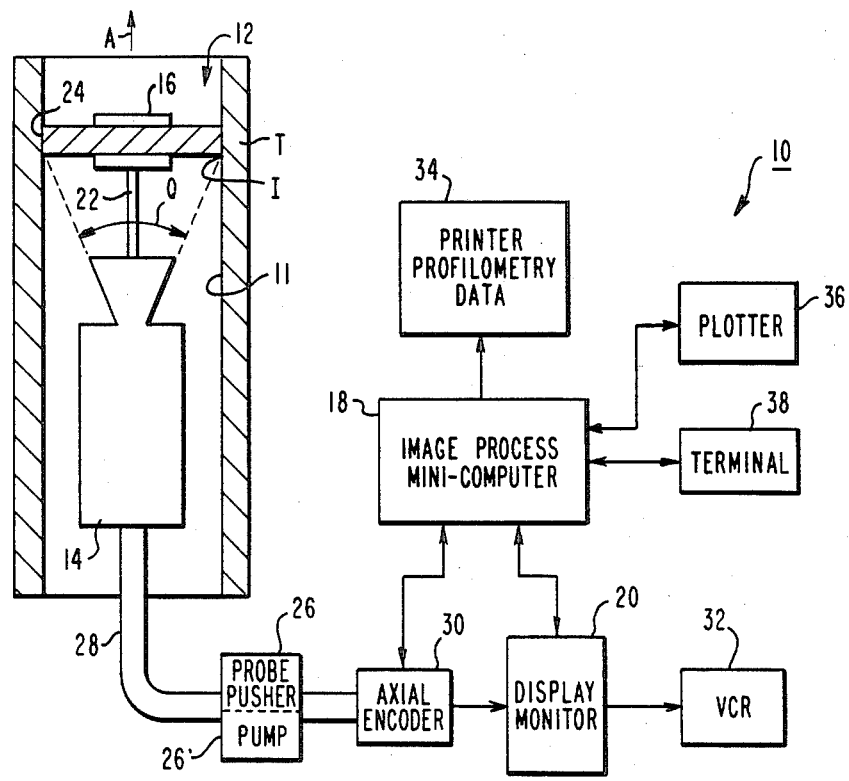
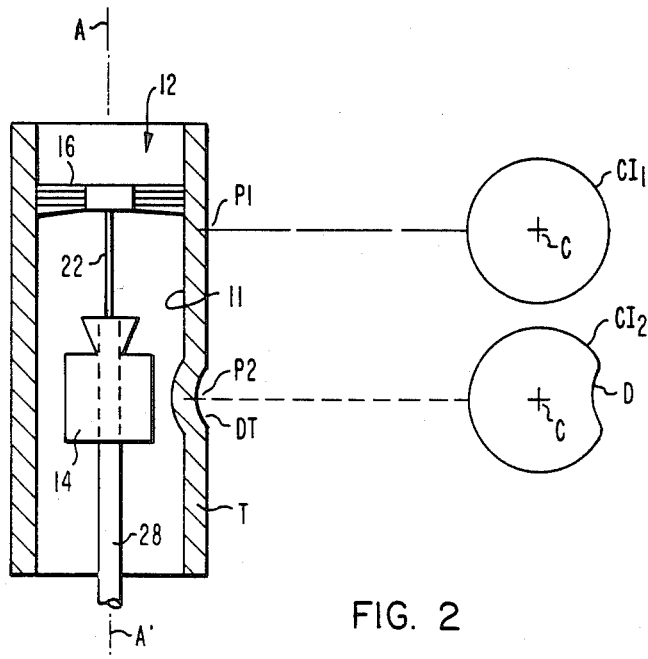
FIG. 1
FIG. 2

OPTICAL PROFILOMETRY SYSTEM FOR TUBULAR PRODUCTS

BACKGROUND OF THE INVENTION

1. Field of the Invention

The invention relates to a method and apparatus for optically inspecting tubular products. More specifically the invention is used for non-destructive periodic inspection of pressure containing heat transfer tubes.

2. Description of the Prior Art

Successful and reliable performance of pressure containing tubular products often requires periodic non-destructive inspection to monitor tubing conditions and ultimately provide the basis for a rational maintenance and repair strategy. In the power generation industry, a number of inspection techniques are used to assess the condition of tubular products used in a wide variety of applications. Often a number of techniques are used to complement each other because of the inherent advantages and limitations associated with virtually all tests. For example, slower yet more descriptive ultrasonic test methods are often used to complement higher speed less quantitative eddy current methods in heat transfer tubing applications. Optical inspection is an important test which offers good credibility. However, optical inspection is rarely practical except in extreme circumstances. Detailed visual inspections are very time consuming, and image interpretation can be difficult under in service conditions even using the most advanced equipment.

Ultra high resolution charged coupled device (CCD) video probe cameras combined with image processing computer capability offer the promise of both rapid and automatic visual examination of tubular products. In reality, however, image processing of in service tubing inspection data is very difficult because of the typical wide variation in range of features and image quality encountered during the visual scan of even a single tube. In many applications, miles of tubing must be examined.

Until the present invention, the promise of rapid and automatic visual inspection has not been realized. In the present invention, visual information may be collected using a technique which complements existing inspection methods. The method provides detailed information yet permits relatively fast inspection of tubing products in the order of one foot per second.

SUMMARY OF THE INVENTION

There has been provided an optical profilometry system comprising means for visually inspecting interior surfaces of tubular objects and simultaneously collecting image analysis data so that direct comparison of data is possible for optimum inspection of the interior surfaces. The system comprises a probe axially moveable in the tubular object, including a video camera having optical sensing means and surface engaging means located in the optical view of the camera for engaging the internal surface of the tubular object to create a contrasting image therewith. The system further includes image processing means responsive to the camera output for creating a data image of the contrasting image and a monitor responsive to the camera output for producing a visual representation of the contrasting image.

In various embodiments axial positioning means has been provided for moving the probe axially of the tubular object. An axial encoder responsive to the position of the camera provides axial correlation data for the image processing means. A data terminal, and various data storage means including a printer, a plotter and a video cassette recorder (VCR) may be used in combination with the image processing means.

The method of the present invention includes locating surface engaging means closely conforming with the internal surfaces of the object to create a contrasting image at the interface of the internal surface and the surface engaging means and viewing the interface with electronic viewing means for providing electronic reproduction of the contrasting image while at the same time analyzing the contrasting image for detecting defects in the surface of the object.

BRIEF DESCRIPTION OF THE DRAWINGS

The invention may be better understood, and further advantages and uses thereof are readily apparent, when considered in view of the following detailed description of exemplary embodiments, taken with the accompanying drawings in which:

FIG. 1 is a schematic illustration of an apparatus for implementing the present invention, including a probe for engaging and viewing the internal surface of a workpiece and an image processing computer and display.

FIG. 2 is a schematic illustration of the probe located within a workpiece having respective damaged and undamaged internal surfaces and further illustrating in ideal form the resulting contrasting images resulting from inspection of the locations.

DESCRIPTION OF THE PREFERRED EMBODIMENTS

Figure 3A:
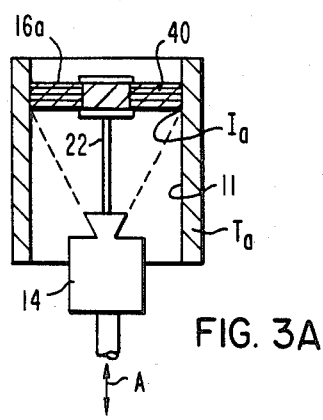
FIGS. 3A–3F are sectional illustrations of exemplary probes having various surface engaging means within the scope of the present invention.

The general configuration of the present invention is best illustrated in FIG. 1. The invention is directed to an optical profilometry system 10 comprising a probe 12 including a camera 14 and a surface engaging means or feeler 16 spaced from the camera. An image process computer 18 is responsive to the camera output, and a display 20 likewise responsive to the camera output allows visual examination of the camera image. The camera 14 and feeler 16 are mounted for axial movement within a hollow workpiece, for example tube T having an internal cylindrical surface 11. In the embodiment of FIG. 1, a connecting rod 22 joins and maintains the camera 14 and feeler 16 in spaced relationship. A surface engaging portion 24 of the feeler 16 is sized to snugly fit within the tube T and engage the internal surface 11 thereof. The interface I between the surface engaging portion 24 and the internal surface 11 is located within a viewing angle Q of the camera 14 which generates a contrasting image CI. (FIG. 2 shows schematic contrasting images $CI_1$ and $CI_2$ which are described hereinafter.)

The camera 14 is moved axially of the tube T by means of a probe pusher 26 cooperating with an elongated interconnecting cable 28. The probe pusher 26 moves the camera 14 and interconnected feeler 16 axially of the tube T in the direction of the arrow A. It should be understood that the probe pusher 26 may be reversed to pull the probe 12 in the opposite direction. Cable 28 may carry internal conductors (not shown) for connecting the camera output to the image processing computer 18.

The position of the cable 28 and hence the probe 12 is detected by axial encoder 30. Information representing the position of the probe 12 may be digitally communicated to the image process computer 18 to thereby correlate the position of the probe 12 with the corresponding contrasting image produced thereby. Thus, sequential contrasting images of the interface I of the tube T and feeler 16 may be stored and correlated in the image process computer 18. The axial encoder 30 may also include means responsive to the image process computer 18 for controlling the probe pusher 26 and thereby locate the probe 12 at a particular position if desired.

The contrasting image CI of the camera 14 is also transmitted to the monitor or display 20 which in turn may be coupled to a video storage device such as a video cassette recorder or VCR 32.

A terminal 38 typical of those used with computers and the like including a keyboard (not shown) may be coupled to the image process computer 18 for providing operator interface with the computer and various controls. A printer 34 and a plotter 36 may be provided as part of the invention to be responsive to outputs of the image process computer 18 for providing hard copies of the profilometry data. The image process computer 18 also includes internal memory (not shown) for storing the data in digital form, for example a large random access memory or another suitable storage device such as a hard or floppy disk (not shown).

FIG. 2 illustrates schematically, resulting exemplary contrasting images produced by the subject invention. For purposes of explanation, it is to be assumed that the camera 14 and the feeler 16 are mechanically coupled by connecting rod 22 and move together along the axial direction A-A' of the tube T. As the camera 14 and feeler 16 are moved in the tube T the interface I between the feeler 16 and the internal wall 11 of the tube T is viewed by the camera 14 which thereby produces a contrasting image of the interface. In FIG. 2 a contrasting image $CI_1$ is produced at axial position P1 of the tube T. In the example shown in FIG. 2, the tube T is circular at position P1. The contrasting image $CI_1$ produced thereby is a regular circle showing litle or no distortion and represents an undamaged tube within tolerance limits which may be set by the user.

As the camera 14 and feeler 16 are moved to axial position P2, a different contrasting image $CI_2$ is produced. This image shown in FIG. 2 shows a rather pronounced dent D which corresponds to a dent or tube distortion DT in the tube T.

The information represented by the contrasting images $CI_1$ and $CI_2$ may be manually or automatically evaluated. Manual anaylsis requires making precise measurements of image features (for example, maximum and minimum diameter), and thereafter making calculations based thereon to determine tube distortion sometimes referred to as denting and ovality.

Denting may be defined as the amount of local distortion as compared with the nominal or undistorted internal diameter (ID) of the tube T according to the following expression:

$$\text{Denting} = \frac{\text{Nom } ID - \text{Min } ID}{\text{Nom } ID}$$

Ovality is defined as the average amount of local distortion as compared with the nominal ID according to the following expression:

$$\text{Ovality} = \frac{\text{Nom } ID - \frac{\text{Max } ID - \text{Nom } ID}{2} + \frac{\text{Nom } ID - \text{Min } ID}{2}}{\text{Nom } ID}$$

Mandrel clatter causes variations in the ID as follows:

$$\text{Mandrel Clatter} = \tfrac{1}{2}(\text{Min } ID + \text{Max } ID)$$

Pitting or erosion of tube ID is defined as follows:

$$\text{Pitting} = \frac{\text{Max } ID - \text{Nom } ID}{\text{Nom } ID}$$

In all of the above expressions:
Nom ID=Norminal or undistorted or specified ID;
Max ID=Largest ID crossing the nominal center C;
Min ID=Smallest ID crossing the nominal center C.

FIGS. 3A-3E represent examples of various embodiments of the feeler 16. In FIG. 3A the feeler 16a comprises a circular brush 16a having radially extending bristles 40 which engage the internal surface 11 of the tube $T_a$ and form the interface $I_a$ therewith. The brush arrangement of FIG. 3A is especially useful in evaluating boiler tubing which is often times corroded and pitted.

Figure 3B:
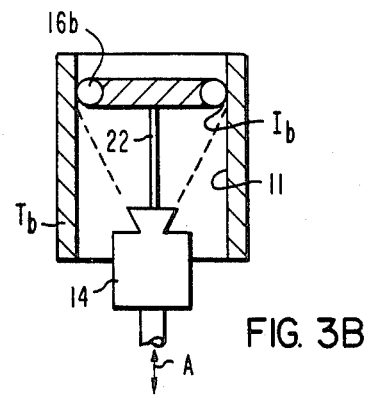

FIG. 3B illustrates an inflatable or resilient bladder 16b in the form of a pancake or torus which forms an interface $I_b$ with the surface 11 of tube $T_a$.

Figure 3C:
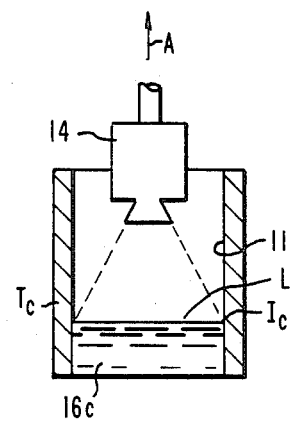

In FIG. 3C the feeler 16c takes the form of a supply of water or liquid which is pumped from a lower end of the tube $T_c$ at a rate sufficient to cause the level L of the liquid 16c to move in the axial direction A at the same rate as the upward movement of the camera 14. An interface $I_c$ formed between the level L of the liquid 16c and the tube surface 11 may thus be viewed by the camera 14 to produce a contrasting image. The liquid 16c may also be a chemo-luminescent oil which gives off its own light to thus enhance the contrast between the tube surface 11 and the feeler 16c.

Figure 3D:
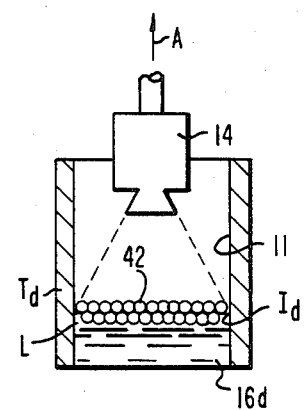

FIG. 3D is similar to FIG. 3C in that a liquid 16d forms part of the feeler. However, particles 42 floating at or about the liquid level L form the interface $I_d$ with the tube surface 11. The particles 42 may be light weight styrofoam beads which provide good contrast in the environment of the tube $T_d$.

In the embodiments shown in FIGS. 3C and 3D it is necessary to modify the control system of FIG. 1 to regulate the liquid level L and account for the axial position of both the liquid level L and the camera 14. A pump 26' (FIG. 1) goeverned by the computer 18 can be used to regulate the liquid level L. Likewise the axial encoder 30 may provide digital liquid level data. The camera 14 may be separately controlled by the probe pusher 26 or alternatively, the camera 14, because it is extremely light weight, may be carried on the liquid level L by means of a small float and connecting rod (not shown).

Figure 3E:
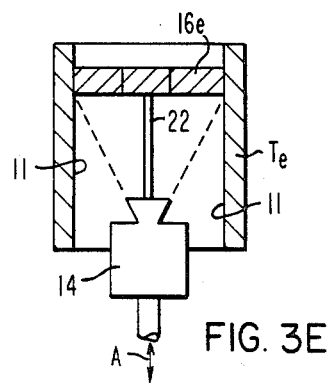

FIG. 3E illustrates a feeler 16e formed of a foam disk which closely conforms to the tube wall 11.

Figure 3F:
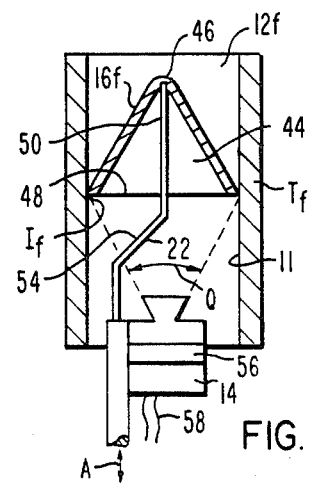

FIG. 3F is an illustration of a probe 12f including a camera 14 and a feeler 16f. The feeler 16f comprises a conical resilient member 44 having a tapered end 46 and a relatively wide open end 48. The open end 48 conforms to the internal surface 11 of the tube $T_f$. Connecting rod 22 has a distal end 50 located in and attached to the tapered end 46. The camera 14 is mounted in a holder 56 secured on the connecting rod 22 beyond offset 54. The camera 14 has its own light source (not shown) and connecting wires 58 coupled to the external equipment (FIG. 1). The embodiment of FIG. 4F was used to produce a good contrasting image discussed hereinafter. The camera 14 is spaced from the open end 48 of the feeler 16f so that the interface $I_f$ between the feeler 16f and the tube $T_f$ lies within the viewing angle Q of the camera 14.

Figure 4A:
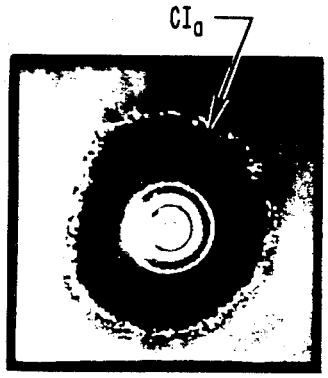
FIGS. 4A–4D are copies of actual contrasting images produced by the camera, the information from which may be either visually inspected or stored in digital or video storage means.
Figure 4B:
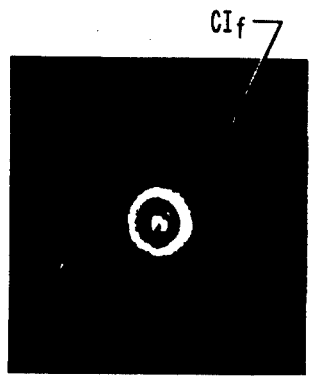

Exemplary contrasting images of some of the various feeler embodiments are illustrated in FIGS. 4A–4E. In FIG. 4A the contrasting image $CI_a$ was produced by the camera 14 in viewing the brush arrangement 16a. The image in FIG. 4A shows a 0.531 inch ID tube having 5% denting and 6.5% ovality. In FIG. 4B the image $CI_4$ was produced by the conical feeler 14f of FIG. 3F. The results are similar to FIG. 4A.

Figure 4C:
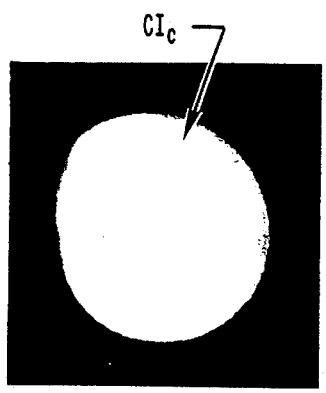

FIG. 4C is a contrasting image $CI_c$ produced by the rising liquid arrangement illustrated in FIG. 3C. The results are similar to FIG. 4A.

Figure 4D:
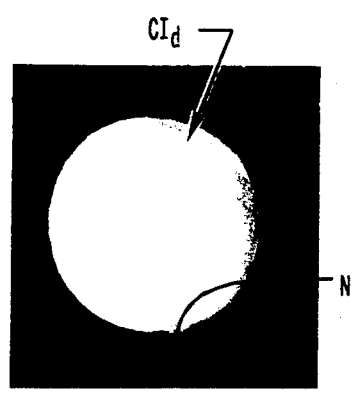

FIG. 4D shows a contrasting image $CI_d$ produced by the rising liquid method of FIG. 3C in which a portion of the internal surface 11 of a 0.531 ID tube T having a calibrated 0.013×0.060 ID inch notch N therein.

As can be observed from an examination of the images reproduced above, highly accurate results may be provided to quantitatively analyze the condition of the tube T at various axial positions. The tubes T may be visually inspected but more importantly the visual inspection may be carried out automatically and at relatively high speed. The results may be viewed and analyzed in real time with instant quantitative results either displayed on the monitor 20 or produced at the printer 34 or plotter 36. Alternatively, a run on a particular tube may be made and the results may be analyzed at a later time. If an alarm sounds, the particular tube may be inspected immediately by returning the camera to the particular axial positions of interest for a real time inspection. If defective, the tube may be repaired, replaced, or plugged while at the same time data may be accumulated in order to determine overall performance of the tubes and the system.

The data produced may be sufficiently comprehensive so that conditions symptomatic of tube or apparatus failure may be detected early enough to prevent, avoid, or minimize catastrophic failure of the system. Data produced as a result of the utility of the present invention makes it possible to quickly and accurately evaluate the condition of tubular objects. It may also be possible using resulting data to accurately and effectively analyze current performance and possibly predict future performance of the equipment under test.

A number of image processing computers and programs exist and are available commercially which can easily convert images such as those represented in FIGS. 4A–4F to extremely accurate profilometry data at near real time conditions. The various components illustrated and described in FIG. 1 for effecting control of the system are known to those skilled in the art and are not discussed in detail herein.

We claim as our invention:

1. An optical profilometry system comprising: means for visually inspecting interior surfaces of tubular objects and simultaneously collecting image analysis data so that direct comparison of data is possible for optimum inspection of the interior surfaces of the tubular objects including:
   probe means including a video camera having optical sensing means axially movable in the tubular object, and surface engaging flexible feeler means located in spaced relation with the camera in the optical view of the camera for adjustably engaging the inner surfaces of the tubular object to create a contrasting image at a particular axial position within said tubular object;
   means for moving the probe means axially of the tubular object and means responsive to the probe means position for producing an output indicative of the axial position of the probe means wihin the tubular object;
   image processing means responsive to the output of the camera and the means responsive to the probe means position for creating a data image of the contrasting image for each selected axial position along the tubular object; and
   monitor means coupled to the camera output for viewing the contrasting image in real time.

2. Means for inspecting and imaging a contour of interior surfaces of a tube comprising a video camera sized to be located interior of the tube and flexible feeler means within the optical path of the camera and sized to engage with and closely conform to the interior surfaces of the tube, and which feeler means adjusts to the contour of the tube along an interface therebetween for creating a contrasting image of the contour at the interface between the tube and feeler means for detection by the video camera.

3. The inspecting and imaging means of claim 2 further comprising image processing computer means coupled to the camera for receiving an output thereof representative of the contrasing image, said image processing computer means including means for producing data in response to the output of the camera corresponding to characteristics of the contrasting image and means for storing the data.

4. The inspecting and imaging means of claim 3 further comprising means for axially positioning the camera and feeler means at selected axial locations within the tube and means responsive to the positioning means and coupled to the image processing computer means for encoding the axial position of each contrasting image.

5. The inspecting and imaging means of claim 2 further including a video monitor coupled to the video camera for producing a real time representation of the contrasting image.

6. The inspecting and imaging means of claim 5 further including video storage means responsive to the camera output for producing a stored reproducable encoded version of the contrasting image.

7. The inspecting and imaging means of claim 2 wherein the feeler means comprises a circular brush having bristles extending radially and sized to closely conform to the interior surface of the tube.

8. The inspecting and imaging means of claim 2 wherein the feeler means includes a resilient bladder sized to closely conform with the interior surface of the tube and creating the contrasting image at the interface therebetween.

9. the inspecting and imaging means of claim 2 wherein the feeler means includes a source of liquid filling a portion of the tube and in which the liquid immediately adjacent the interior surface of the tube forms the contrasting image at the liquid tube surface interface.

10. The inspecting and imaging means of claim 9 wherein the liquid is a chemo-luminescent oil for producing its own illumination to thereby enhance the contrast between the tube surface and the feeler.

11. The inspecting and imaging means of claim 9 wherein the feeler means further includes floating particulate material located at the liquid level for enhancing the contrasting image at the interface between the liquid and interior surface of the tube.

12. The inspecting and imaging means of claim 2 wherein the feeler comprises a circular disk of foam-like material having a radial extent sufficient to closely conform the disk with the interior surface of the tube.

13. The inspecting and imaging means of claim 2 wherein the feeler comprises a resilient conical member having a relatively small tapered end and a relatively large open circular end for engaging the internal surface of the tube.

14. The inspection and imaging means of claim 2 further including an axial encoder responsive to the position of the camera within the tube for producing an output in digital form, which output is coupled to the image processing computer for correlating the contrasting image with the selected axial position thereof.

15. The inspection and imaging means of claim 2 wherein said TV camera is a miniature charge coupled device.

16. A method of inspecting and imaging a contour of interior surfaces of tubular objects comprising the steps of locating surface engaging flexible feeler means closely and adjustably conforming with the interior surfaces of the tubular object to create along an interface therebetween a contrasting image at the interface of the feeler means and the interior surfaces; viewing the interface of the feeler means and the internal surfaces with electronic viewing means and producing an electronic reproduction of the contrasting image; analyzing the electronic reproduction of each contrasting image for detecting defects in the object which defects are departures from selected dimensional characteristics of the tubular object.

17. The method of claim 16 further including viewing the interface between the feeler and internal surfaces of the tube by means of a video monitor in real time.

18. The method of claim 16 further including analyzing the contrasting image by means of image analysis computer means including means for producing data corresponding to the contrasting image and means for storing the data.

* * * * *